(12) United States Patent
Summerville et al.

(10) Patent No.: US 8,277,409 B2
(45) Date of Patent: Oct. 2, 2012

(54) CUTTING ELEMENT FOR A RETRACTING NEEDLE SYRINGE

(75) Inventors: Andrew G. Summerville, Goshen, CT (US); Jon D. Swenson, Wayne, NJ (US); Christina Joy D'Arrigo, Hoboken, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 1921 days.

(21) Appl. No.: 11/294,256

(22) Filed: Dec. 5, 2005

(65) Prior Publication Data

US 2007/0129675 A1 Jun. 7, 2007

(51) Int. Cl.
*A61M 5/00* (2006.01)

(52) U.S. Cl. ........................................ 604/110

(58) Field of Classification Search .................. 604/110, 604/181
See application file for complete search history.

(56) References Cited

U.S. PATENT DOCUMENTS

| | | | | |
|---|---|---|---|---|
| 2,590,900 A * | 4/1952 | Sommerstein | ............... | 604/415 |
| 3,667,657 A * | 6/1972 | Chiquiar-Arias | ............... | 222/80 |
| 3,951,146 A * | 4/1976 | Chiquiar-Arias | ............. | 604/110 |
| 3,998,224 A * | 12/1976 | Chiquiar-Arias | ............. | 604/110 |
| 4,696,308 A * | 9/1987 | Meller et al. | ................... | 600/567 |
| 4,710,170 A * | 12/1987 | Haber et al. | ................... | 604/110 |
| 4,925,216 A * | 5/1990 | Steer | ................ | 285/3 |
| 5,423,756 A * | 6/1995 | van der Merwe | ............. | 604/110 |
| 5,527,284 A * | 6/1996 | Ohnemus et al. | ............. | 604/110 |
| 5,562,624 A * | 10/1996 | Righi et al. | .................. | 604/110 |
| 5,935,104 A * | 8/1999 | Janek et al. | .................. | 604/110 |
| 6,139,526 A * | 10/2000 | Bedner et al. | ................. | 604/110 |
| 6,413,237 B1 * | 7/2002 | Caizza et al. | .................. | 604/110 |
| 6,419,684 B1 * | 7/2002 | Heisler et al. | ................. | 606/170 |
| 6,432,087 B1 * | 8/2002 | Hoeck et al. | .................. | 604/181 |
| 6,517,516 B1 * | 2/2003 | Caizza | .......................... | 604/110 |
| 6,679,863 B2 * | 1/2004 | Bush et al. | ................... | 604/181 |
| 6,689,106 B2 * | 2/2004 | Bush et al. | ................... | 604/181 |
| 6,712,787 B1 * | 3/2004 | Dysarz | .......................... | 604/110 |
| 2004/0059294 A1 * | 3/2004 | Pelkey et al. | ................. | 604/110 |
| 2007/0100293 A1 * | 5/2007 | Cipoletti et al. | .............. | 604/218 |
| 2007/0244433 A1 * | 10/2007 | Kiehne | ......................... | 604/110 |
| 2008/0097308 A1 | 4/2008 | Schiller et al. | | |
| 2008/0300550 A1 | 12/2008 | Schiller et al. | | |

OTHER PUBLICATIONS

PCT International Search Report for PCT/US06/46139, (Sep. 13, 2007), 2 pgs.
PCT International Preliminary Report on Patentability in PCT/US06/046139, (Sep. 13, 2007), 6 pgs.

* cited by examiner

*Primary Examiner* — Nicholas Lucchesi
*Assistant Examiner* — Aarti B Berdichevsky
(74) *Attorney, Agent, or Firm* — Diehl Servilla LLC

(57) ABSTRACT

A cutting element for a retracting needle syringe having a plunger with a cuttable distal end and a spring biased needle held by a cuttable support and a cutting element capable of cutting the cuttable distal end and the cuttable support includes a body portion having a proximal end, a distal end side wall therebetween and a passageway therethrough. The distal end of the body portion includes a cutting edge and a raised distally projecting tapered cutting tooth having distally converging edges. At least one tooth edge includes a sharp side wall for cutting the distal end of the plunger and the needle support.

3 Claims, 17 Drawing Sheets

CUTTING ELEMENT FOR A RETRACTING NEEDLE SYRINGE

FIELD OF THE INVENTION

The present invention relates to syringes and needle assemblies. More particularly, the present invention relates to a cutting element for a syringe and needle assembly having structure allowing for the withdrawal of the needle cannula into the syringe barrel after use.

BACKGROUND

In recent years there has developed an increased concern regarding the transfer of disease, infection and the like to syringe users and healthcare professionals who accidentally or through negligent handling, stick themselves with hypodermic needles while disposing of used hypodermic needle. In many areas in a hospital, where needle cannula products are used, disposal bins are provided so that a syringe or other needle cannula product may be immediately discarded in a safe rigid container. However, there are areas of medical practice, such as emergency rooms, where disposal containers may not be readily available or practical, and where products having self-contained safety features are desirable. In theory, after such a syringe is used to inject medication or for another purpose, a safety device contained within the syringe or needle assembly is activated to prevent further contact with the sharp needle tip. One type of safety syringe includes structure which allows the withdrawal of the hypodermic needle into the syringe barrel to minimize the chance of further contact with the sharp needle tip.

The prior art includes retracting needle syringes which include a spring loaded needle assembly which is held in position during normal use of the syringe assembly and a hollow plunger rod which is sealed during normal use of the syringe assembly so that medication or other liquids may not enter the plunger rod cavity. These syringes must have structure to allow release of the spring-loaded needle and the opening of the plunger rod cavity so that the needle may enter the plunger rod cavity after the syringe is used for its intended purpose. To function properly, the cavity in the plunger rod must be sealed so that medication cannot enter into the plunger rod during use. This seal must sometimes withstand high hydraulic pressures when injecting relatively viscous medication through small needles and still be capable of being easily unsealed and to allow access by the needle assembly. Likewise, the needle assembly must be firmly held in place through the forces of injection and still be disengageable so that it may retract into the syringe barrel and into the plunger rod. Some of the prior art retracting needle syringes to solve these problems by providing a leak-proof physical structure for holding the spring-loaded needle in position and for sealing the end of the hollow plunger rod. Upon completion of the injection process additional distally directed force is applied to the plunger causing an internal cutting element to cut through the end of the hollow plunger rod and the support for the spring-loaded needle. In some embodiments, the prior art retracting needle syringe cutter cuts in a proximal direction through the support for the spring-loaded needle assembly and then through the distal end of the plunger rod. In both cases this allows the spring-loaded needle to enter the cavity in the plunger helping to keep the user safe from accidental needle sticks.

Prior art retracting needle syringes that rely on dislodgeable elements or the breaking of frangible barriers will allow the spring-loaded needle to enter into the plunger can require a broad range of forces to disengage the spring-loaded needle. Retracting needle syringes with the cutter have an inherent advantage of being capable of being made so that the forces necessary to activate the retracting needle are more consistent from syringe to syringe.

The present invention addresses an improved cutting element for a retracting needle syringe for providing even more consistent syringe to syringe activation forces and, if desired, lower activation forces.

SUMMARY OF THE INVENTION

A cutting element for a retracting needle syringe having a plunger with a cuttable distal end and a spring biased needle held in an energized state by a cuttable support is provided. The cutting element is capable of cutting the cuttable distal end of the plunger and the cuttable support. The cutting element includes a body portion having a proximal end, a distal end, a side wall therebetween defining a longitudinal axis and a passageway therethrough. The distal end of the body portion includes a cutting edge and a raised distally projecting tapered tooth having a distal tip and distally converging edges. At least one tooth edge includes a sharp side for cutting the distal end of the plunger and the support.

The sharp side wall may include a beveled edge. The cutting element may include a plurality of cutting teeth which may or may not be equally spaced around the distal end of the body portion. The distally converging edges of the cutting tooth may meet to form a distally directed point or not meet and define a distally directed edge at the distal tip.

The cutting element may be configured so that the cutting teeth include two sharp sides for cutting. The cutting teeth may be separated by concave cutting edges running along the distal end of the body portion.

For cutting elements having two or more teeth, the cutting edges between the cutting teeth may be about the same height when measured along the longitudinal axis or the cutting edges may be at different heights when measured along the longitudinal axis of the cutting element.

For cutting elements having two or more teeth, the distal tips of each cutting tooth may be about the same height when measured along the longitudinal axis or the distal tips may be at different heights when measured along the longitudinal axis of the cutting element.

The body portion of the cutting element may be cylindrically shaped. Further, the cutting element configured so that it has three teeth or four teeth.

The cutting element is desirably made of metal and preferably made of stainless steel.

In another embodiment of the present invention the cutting element for a retracting needle syringe having a plunger with a cuttable distal end and a spring-biased needle held in an energized state by a cuttable support is provided. The cutting element is capable of cutting the cuttable distal end of the plunger and the cuttable support. The cutting element includes a cylindrically shaped sheet metal body portion has a proximal end, a distal end, a side wall therebetween defining a longitudinal axis and a passageway therethrough. The distal end of the body portion includes a beveled cutting edge and at least three (3) distally projecting tapered cutting teeth having a distal tip and distally converging beveled cutting edges meeting to form a distally directed point at the distal tip for cutting. The beveled cutting edge on the distal end of the body portion is concavely shaped in the spaces between the teeth which are substantially equally spaced around the distal end of the body portion.

DETAILED DESCRIPTION

Figure 1:
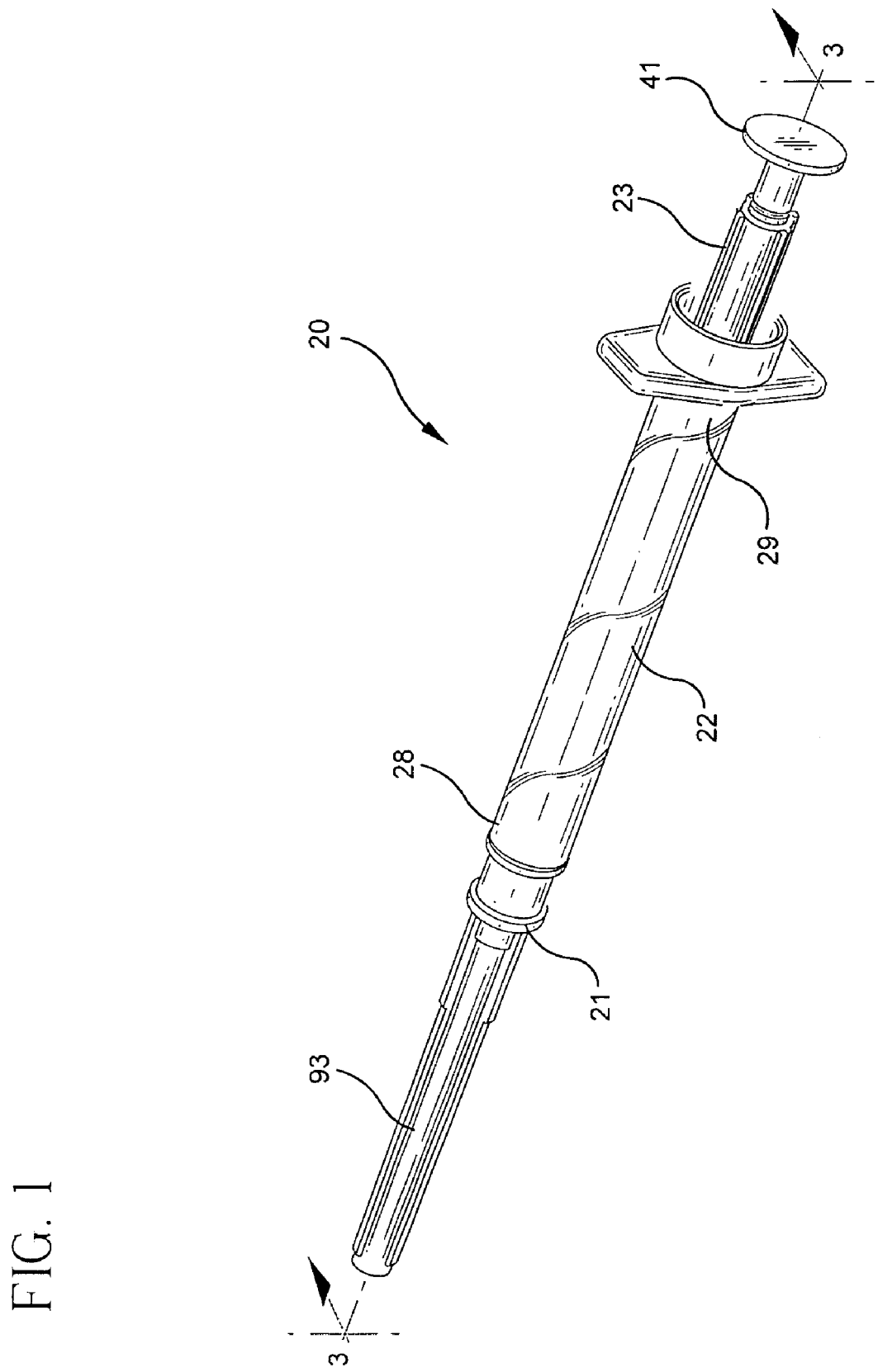
FIG. 1 is a perspective view a the retracting needle syringe.
Figure 2:
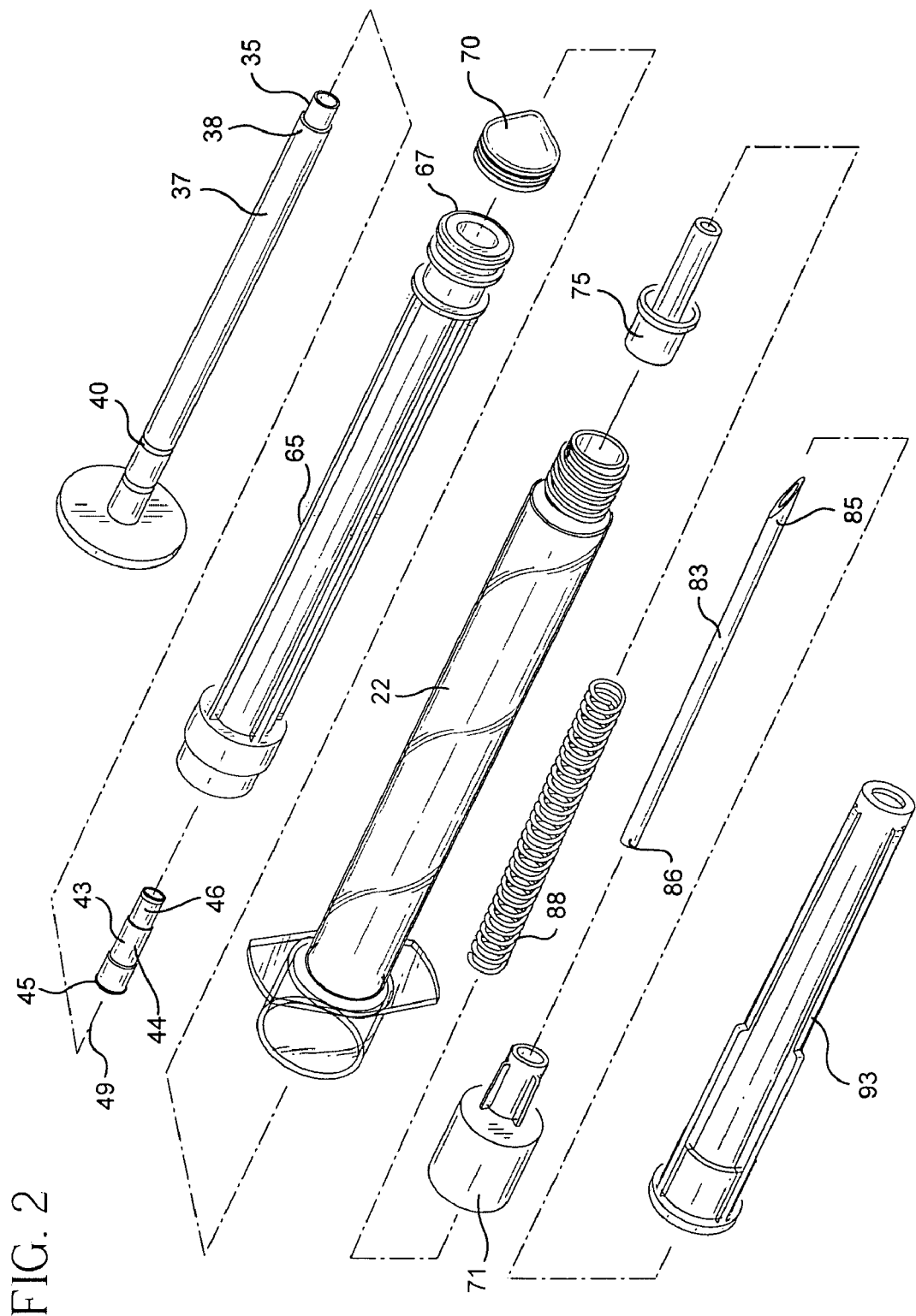
FIG. 2 is an exploded perspective view of the retracting needle syringe of FIG. 1.
Figure 3:
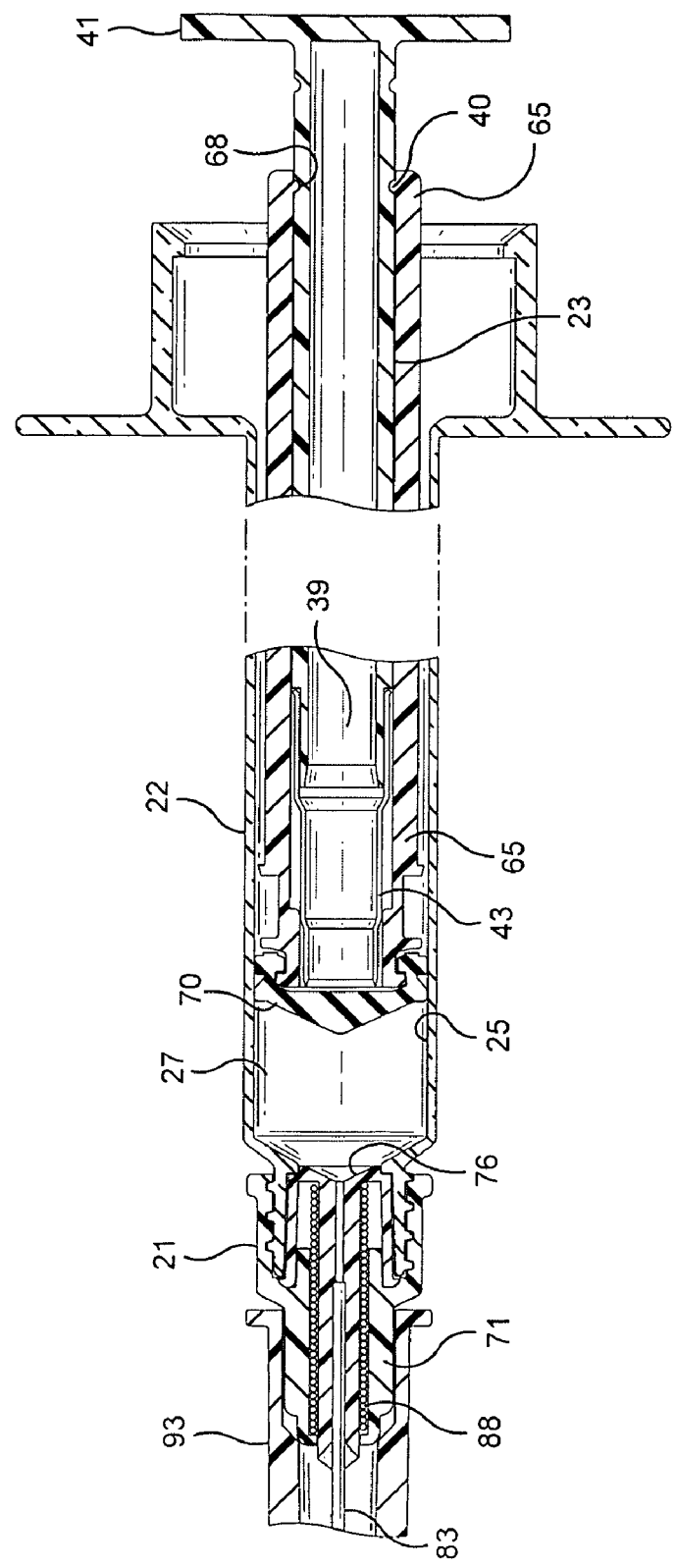
FIG. 3 is a cross-sectional view of the retracting needle syringe of FIG. 1 taken along line 3-3.
Figure 4:
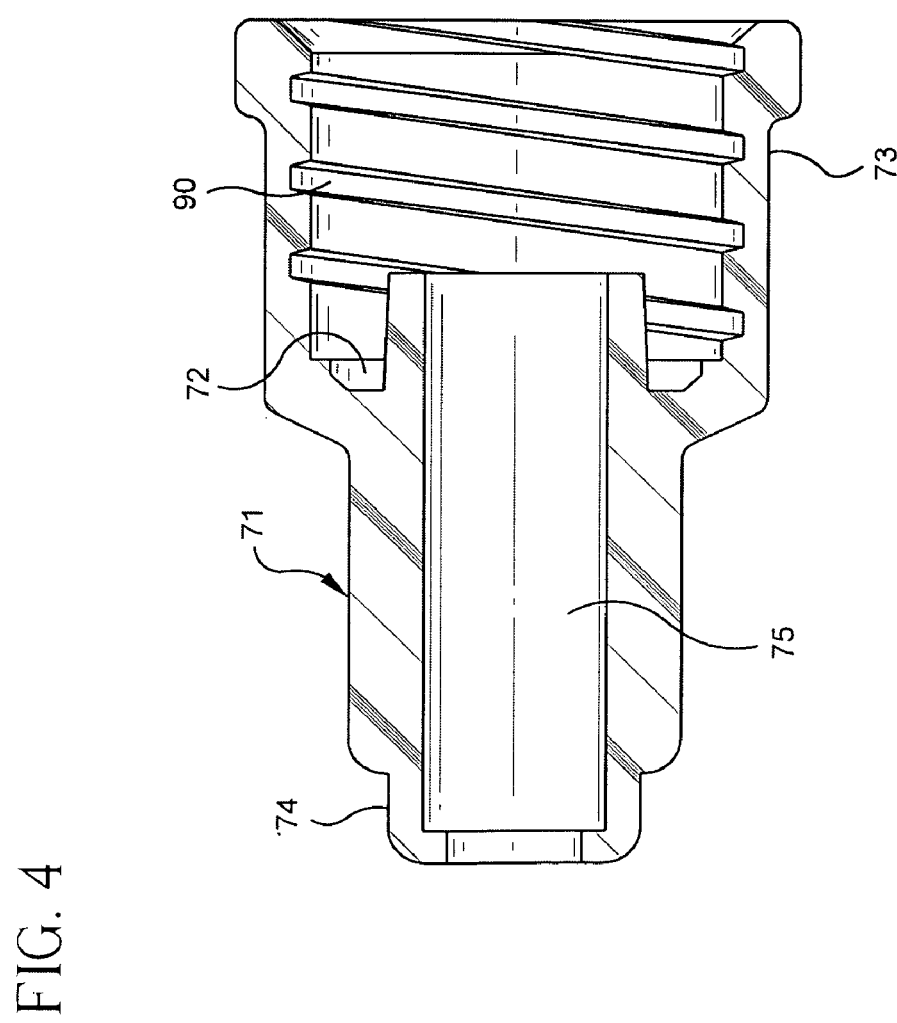
FIG. 4 is an enlarged cross-sectional view of the outer hub of the retracting needle assembly.
Figure 5:
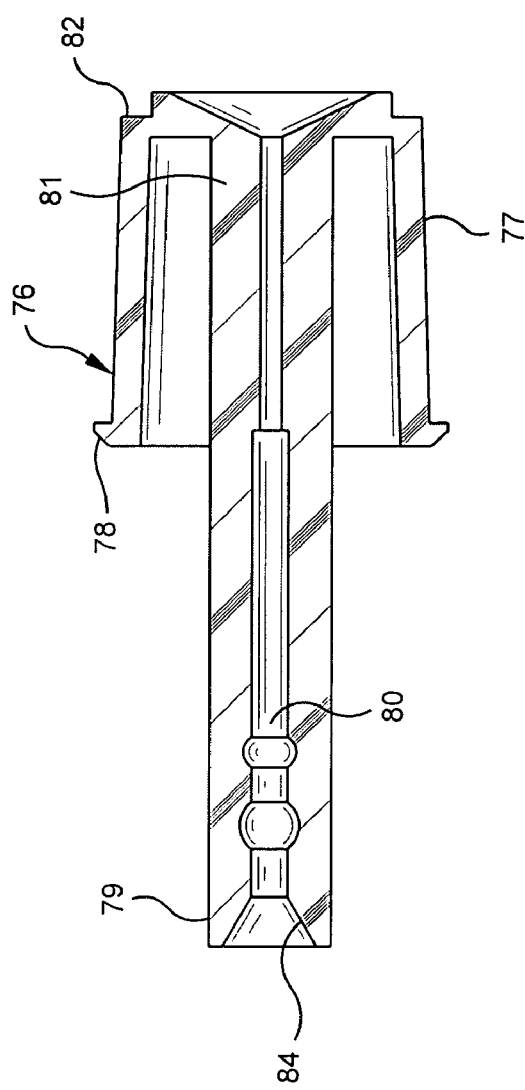
FIG. 5 is an enlarged cross-sectional view of the inner hub of the retracting needle assembly.
Figure 6:
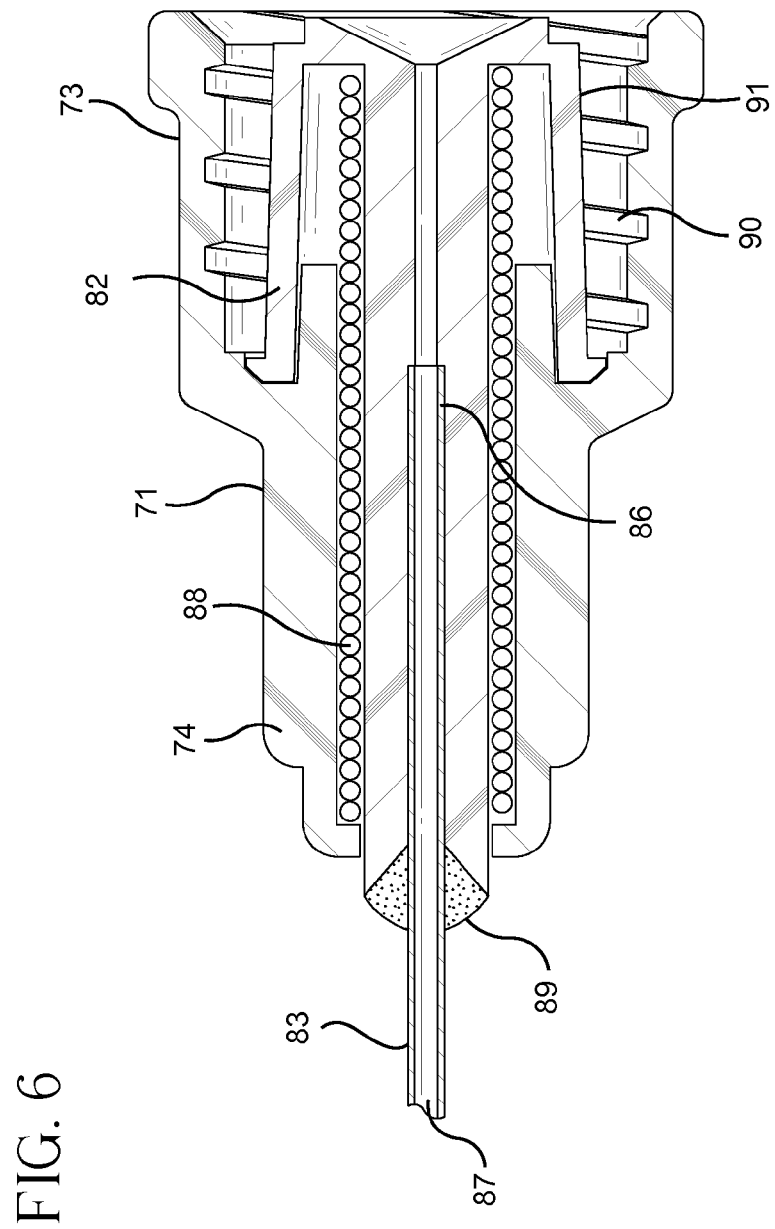
FIG. 6 is an enlarged cross-sectional view of the retracting needle assembly.
Figure 7:
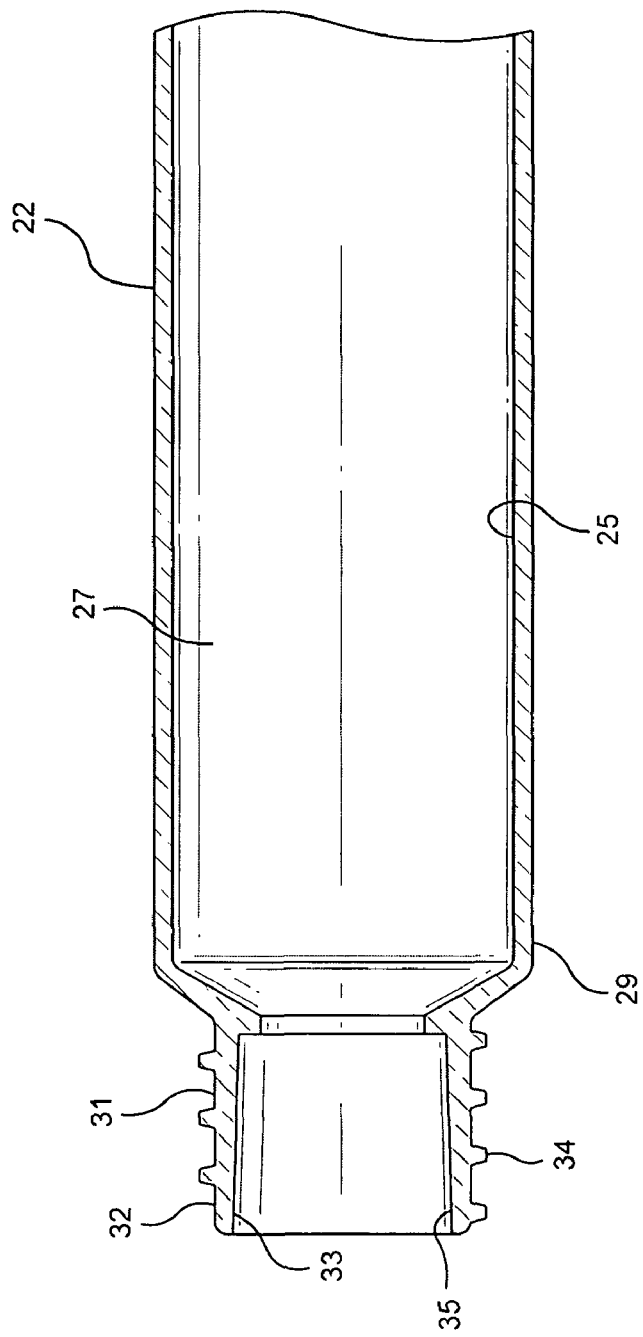
FIG. 7 is an enlarged cross-sectional view of the distal end of the syringe barrel.

While this invention is satisfied by embodiments in many different forms, there are shown in the drawings and will herein be described in detail, preferred embodiments of the invention with the understanding that the present disclosure is to be considered exemplary of the principles of the invention and not intended to limit the scope of the invention to the embodiments illustrated. The scope of the invention will be measured by the appended claims and their equivalents.

Referring to FIGS. 1-17, an operable retracting needle syringe 20 includes a retracting needle assembly 21, a syringe barrel 22 and a plunger 23. The barrel includes an inside surface 25 defining a chamber 27, an open proximal end 28 and a distal end 29 including a cylindrical collar 31 having an outside surface 32 and an inside surface 33.

The plunger is slidably positioned in fluid-tight engagement with the inside surface of the barrel. The plunger preferably includes a proximal portion 37 having a distal end 38 with an elongate cavity 39 therein.

Figure 13:
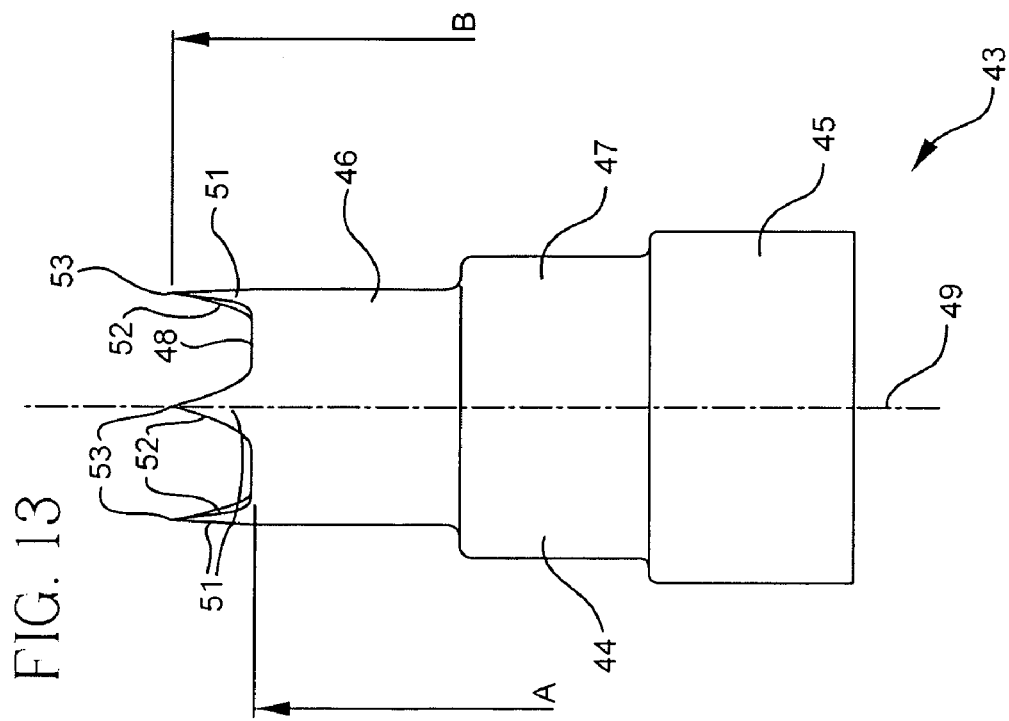
FIG. 13 is a side-elevational view of a cutting element of the present invention.

A cutting element 43 is positioned at distal end 38 of the proximal portion of plunger 23. Cutting element 43 includes a body portion 44 having a proximal end 45, a distal end 46, a side wall 47 therebetween defining a longitudinal axis 49 and a passageway 50 therethrough. Distal end 46 includes a cutting edge 48 and at least one raised distally projecting tapered cutting tooth 51 having a distal tip 53 and distally converging edges 52. At least one tooth edge includes a sharp side wall 55. The tooth cutting element is an important feature of the present invention which offers advantages over prior art cutting elements having a planar cutting edge perpendicular or at an angle to the longitudinal axis of the cutting element. This advantage will be discussed in more detail hereinafter. As best illustrated in FIG. 13, the distal tip 53 of each of the cutting teeth is preferably about the same height when measured along the longitudinal axis as indicated by the letter B. Further, cutting edges 48 may or may not be at the same height when measured along the longitudinal axis. In this embodiment, cutting edges 48 are at substantially the same height, as indicated by the letter A, when measured along the longitudinal axis.

A hollow distal portion 65 of plunger 23 is releasably connected to proximal portion 37 and capable of telescopic motion with respect to the proximal portion. A cover element on the distal portion seals a distal end 67. In this embodiment the cover element is stopper 70. It is preferred that the cover element be made of an elastomeric material selected from the group of thermoplastic elastomers, natural rubber, synthetic rubber and combinations thereof. The cover element can also be thermoplastic or a combination of thermoplastic support material and elastomeric material.

Retracting needle assembly 21 includes an outer hub 71 having a proximal end 73, a distal end 74 and a passageway 75 therethrough. The retracting needle assembly also includes an inner hub or cuttable support 76 having a proximal end 77, a distal end 79 and a conduit therethrough 80. The inner hub includes an inner portion 81 and a cuttable outer portion 82 connected to the inner portion. The cuttable outer portion of the inner hub is connected to outer hub 71. Distal end 79 of the inner hub is smaller than passageway 75 of the outer hub at distal end 74 and is accessible therefrom and preferably projects distally outwardly therefrom.

A needle cannula 83 having a distal end 85, a proximal end 86 and a lumen 87 therethrough. The proximal end of the cannula is connected to distal end 79 of the inner hub so that the lumen is in fluid communication with conduit 80 of the inner hub. The distal end of the cannula preferably includes a sharp or sharpened distal tip.

An energized spring is contained between the outer and inner hubs and this preferred embodiment the energized spring is a compressed coil spring 88. Various spring types and elastomeric materials and the like can be used to provide a biasing force between the inner and outer hubs with the coil spring being merely representative of these many possibilities all of which are within the purview of the present invention. A coil spring is preferred because of its compact size and the ability to easily design the spring to provide the forces necessary for proper operation of the retractable needle assembly.

During assembly the coil spring is placed over the inner portion of the inner hub and then the distal end of the spring is positioned in the outer hub and the inner and outer hubs are moved toward each other to compress the spring and lock together through the action of annular locking projection 78 on the inner hub and annular locking recess 72 in the outer hub. When the inner hub and outer hub are joined, compressing the coil spring, annular locking projection on the inner hub snaps into annular locking recess 72 in the outer hub. The projection and the recess are shaped so that much less force is required to assemble the components than to reverse the process, thus providing for a permanent locked condition wherein the inner hub and the outer hub are inseparable during normal operating conditions. There are numerous ways to connect the inner and outer hub and the snap-fit arrangement taught herein is merely representative of all of these methods which are within the purview of the present invention. In particular, adhesives, separate metal locking clips, ultrasonic welding, crimping, internally molded locking structure and the like can be used to hold the inner hub and the outer hub together.

A preferred way to connect the needle cannula to the retracting needle assembly is to place the proximal end of the needle cannula into the distal end of conduit 80 of the inner hub. An enlarged or irregular portion 84 at the distal end of conduit 80 provides a space for adhesive 89 to be placed around the outside of the needle cannula after it is positioned in the conduit.

The retracting needle assembly also includes means for connecting the outer hub to the collar of the syringe barrel. In this embodiment, means for connecting includes structure providing for threadable engagement between the collar and the outer hub. In this preferred embodiment the structure for threadable engagement includes at least one thread 90 in passageway 75 of outer hub 71 and at least one thread 34 on outside surface 32 of the cylindrical collar. Thus the needle assembly, in this embodiment, is removably connected to the barrel. This feature allows flexibility to interchange needle assemblies and syringes to obtain an appropriately sized needle and syringe combination for the desired drug type and injection site. In addition, the structure of this embodiment allows the installation and removal of the needle assembly from the barrel using the same motions required for installation and removal of a standard hypodermic needle from a standard hypodermic syringe so that no additional training is required for the health care worker.

The structure for threadable engagement between the collar and the outer hub can include a wide variety of thread-like and bayonette-type structures including a thread on the outside surface of the collar and a thread follower projection on the inside surface of the outer hub which will follow the collar thread as the hub is screwed onto the collar. This structure is similar to the well-known locking luer-type needle assembly and syringe combinations wherein the syringe collar has a thread on its inside surface and the needle assembly has two outwardly directed projections on the base of its hub for allowing the hub follow the threads of the collar as it is screwed onto the luer tip and collar. Also, the inside of the collar can be threaded in the outside of the outer hub can have thread followers.

It is also within the purview of the present embodiment to include means for connecting the outer hub to the collar which is permanent rather than removably engageable. For example, the outer hub can be attached to the collar using adhesive or ultrasonic welding, retaining clips or a one-way snap-fit arrangement that renders the assembly irreversible under normal use. Such structures fall within the purview of the prevent invention.

It should be noted that the needle assembly need not be removable or separate from the barrel. Elements of the barrel and the needle assembly can be optimized to reduce the number of parts and achieve a permanently attached needle assembly.

To help prevent leakage, this embodiment includes tapered cylindrical surface 91 on inner hub 76 and tapered cylindrical surface 35 on the inside of cylindrical collar 31 of the barrel. When the retracting needle assembly engages the collar of the barrel, the tapered cylindrical surface 35 on the collar engages tapered cylindrical surface 69 on the inner hub to seal the interface between the hub and the collar to prevent leakage during normal use. A gasket may also be used to seal some portion of the contact surfaces between the needle assembly and the barrel.

Figure 8:
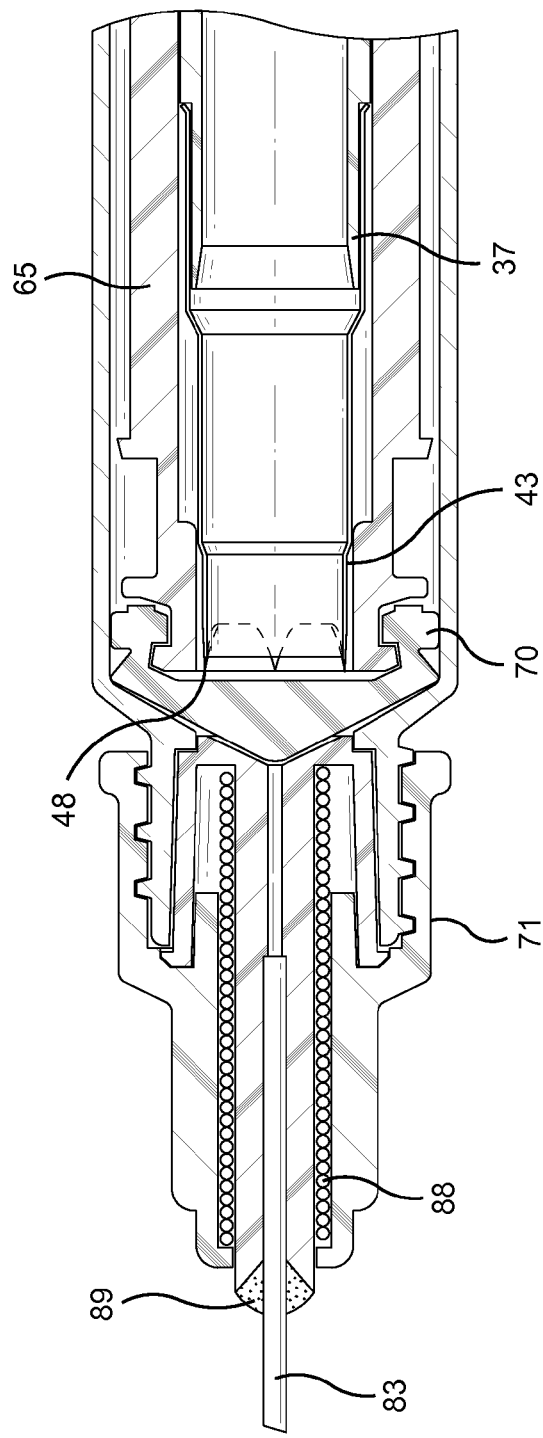
FIG. 8 is a cross-sectional view of the distal end of the retracting needle syringe of FIG. 1 illustrating the syringe after the liquid contained therein has been delivered.
Figure 9:
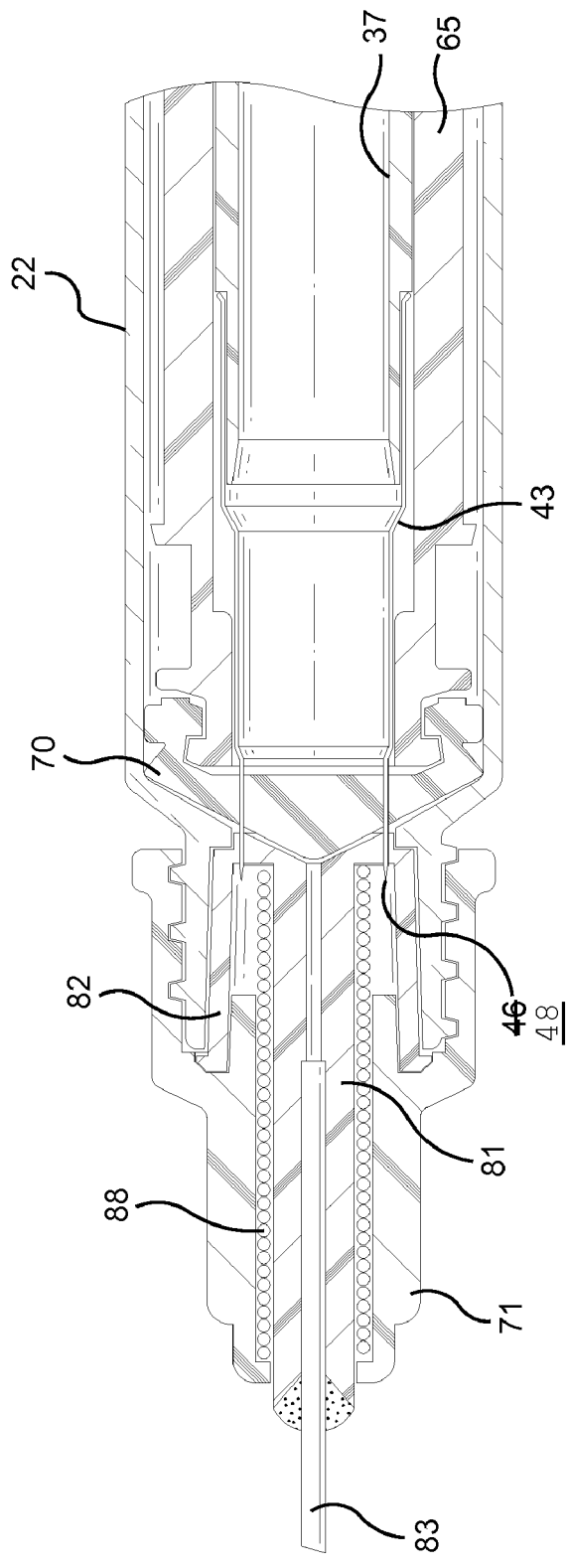
FIG. 9 illustrates the syringe of FIG. 8 when the proximal and distal portions of the plunger rod have separated and the cutting element has cut through the stopper and the inner hub.
Figure 10:
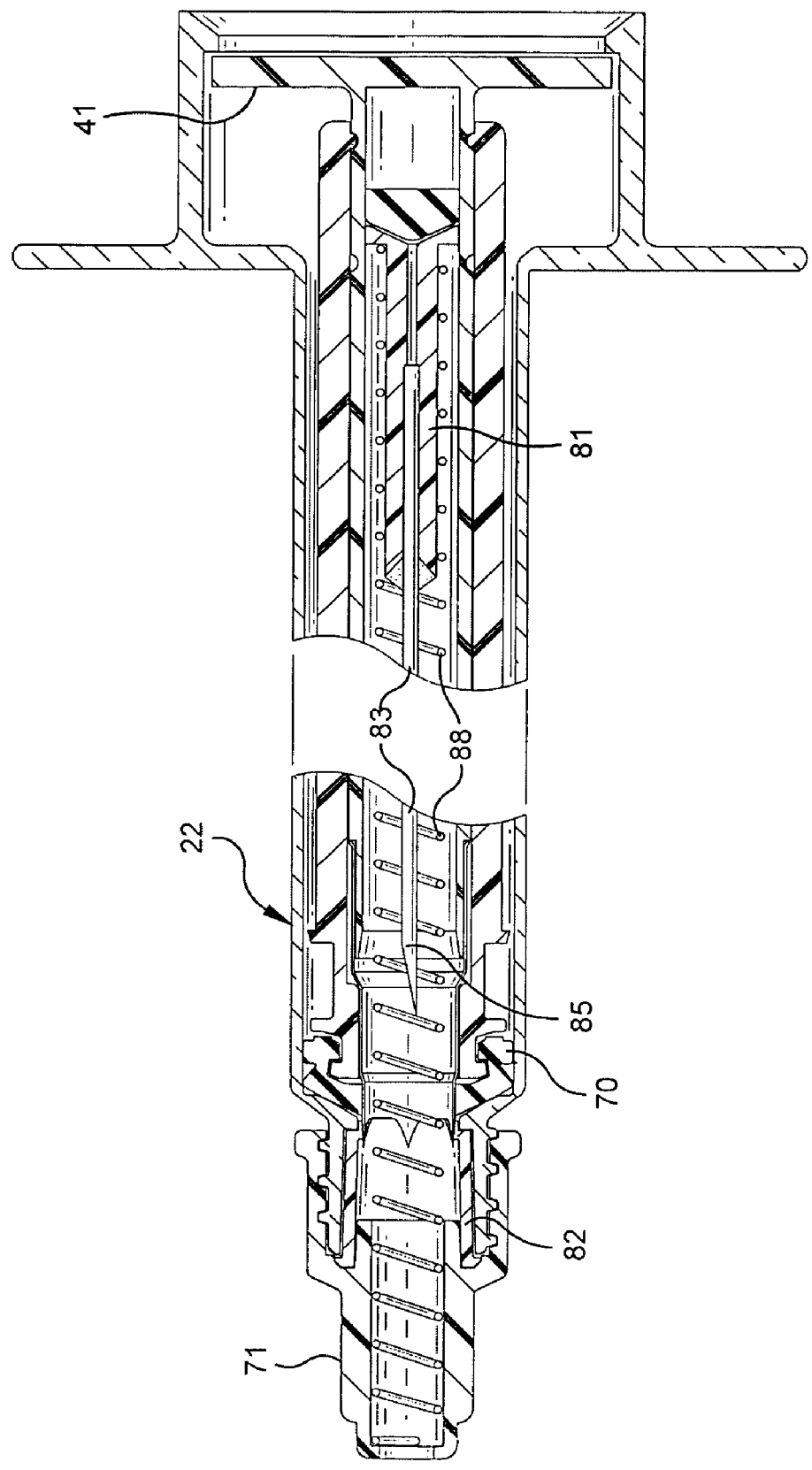
FIG. 10 illustrates the syringe of FIG. 9 when the cutting element has cut completely through the inner hub and the needle has retracted into the plunger.

In use, the retracting needle assembly of the present invention can be removably connected to syringe barrel 22 containing plunger 23. A needle shield 93 can now be removed from the retracting needle assembly thus exposing the needle cannula for use. The retracting needle syringe can be filled, using known methods for such uses as withdrawing injectable liquid from a vial having a pierceable stopper. A syringe may then be used to inject liquid into a patient, an I.V. set, a catheter or other suitable device. After the liquid in the chamber is injected or otherwise delivered, the distal end of the stopper will be contacting the distal end of the barrel chamber as best illustrated in FIG. 8. At this point, the user can apply additional distally directed axial force to the proximal end of the plunger through proximal flange 41 to bottom out the stopper on the distal end of the barrel chamber and to cause the disengagement of the proximal portion 37 of the plunger from distal portion 65 of the plunger. Because the connection between the proximal portion of the plunger and the distal portion of the plunger is broken or overcome, the proximal portion will move distally within the distal portion and along the barrel advancing cutting element 43 so that its sharp distal end will press on and cut through stopper 70 and through the inner hub between inner portion 81 and cuttable outer portion 82, as best illustrated in FIG. 9. Application of a distally directed force to the plunger which causes the release element to cut completely through the inner hub, will allow the spring to propel the inner portion of the inner hub along with the needle cannula into the elongate cavity of the plunger as best illustrated in FIG. 10. The used needle cannula is now safely contained within the syringe assembly and ready for safe disposal.

In this embodiment the releasable connection between proximal portion 37 of the plunger and distal portion 65 of the plunger which allows the telescopic relative motion between the two plunger portions is provided by a snap-fit arrangement between the proximal portion of the plunger and the distal portion of the plunger. In particular, an annular projection 68 on the inside of the proximal end of the distal portion 65 of the plunger engages an annular groove 40 on the proximal end of proximal portion 37 of the plunger. When sufficient axial force is applied, annular projection 68 disengages from annular groove 40 allowing the distal end of the release element to cut through the stopper and the inner hub between the cuttable outer portion and the inner portion. There are numerous structures and materials and elements which can provide for a releasable connection between the proximal and distal portions of the plunger with the structure taught hereinabove being merely representative of the many possibilities all of which are within the purview of the present invention. In particular, any combination of projections and/or recesses and/or discontinuities on the proximal portion and the distal portion can accomplish a similar result. Also, the connection can also be breakable as well as disengageable such as by use of a frangible adhesive between the two elements or molding the elements as an integral structure containing a brittle plastic projection or projections which join the elements and can be broken with a force applied to the plunger. A breakable connection can also be made by connecting the elements with a sheer pin. A sheer pin made be made of plastic with one or more notches or stress risers suitably placed to cause breaking at the desired force levels. A breakable connection may also be accomplished similar to the snap fit arrangement but designing the various projections and recesses to fail upon reaching the desired stress level. Also, it should be noted that a one-piece plunger is possible if the stopper is designed to deflect into a fixed cutting element when excess force is applied to the plunger.

Figure 12:
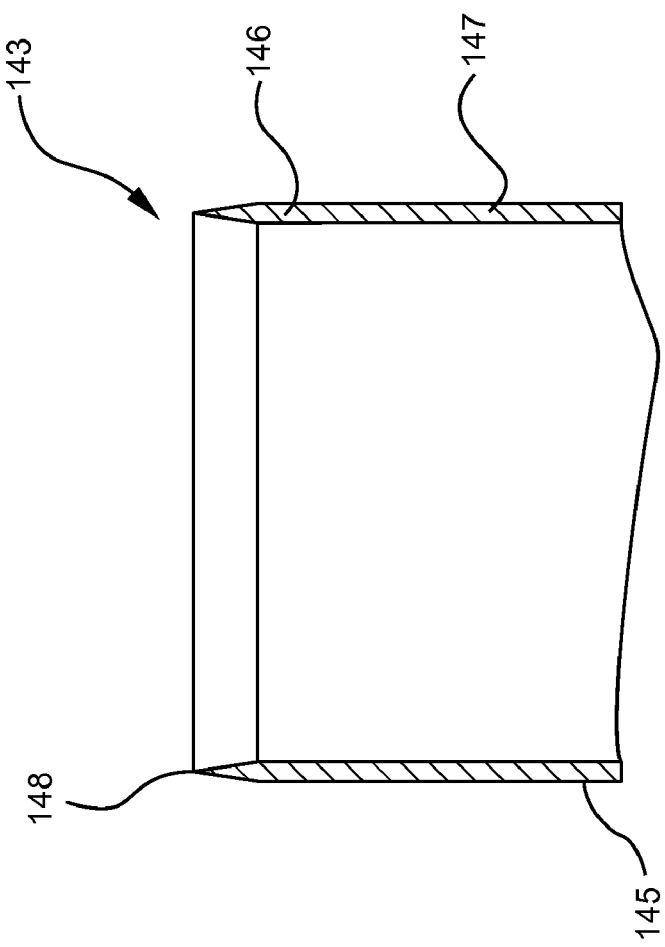
FIG. 12 is a side-elevational view of the cutting element of FIG. 11.
Figure 11:
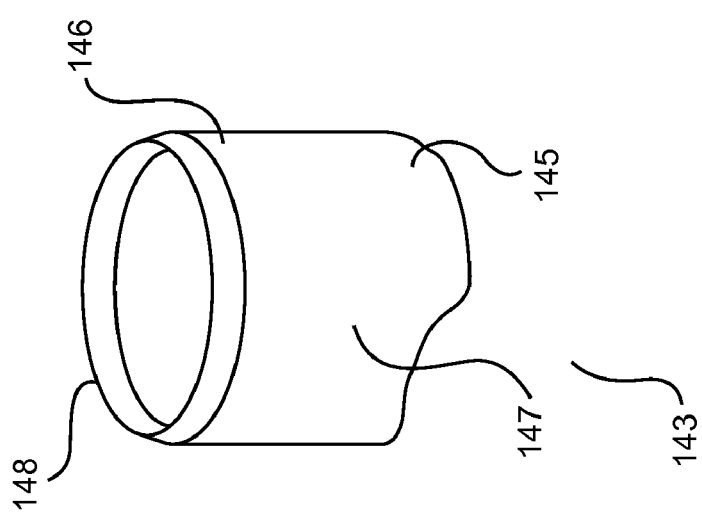
FIG. 11 is a perspective view of a prior art cutting element for retracting needle syringe.
Figure 14:
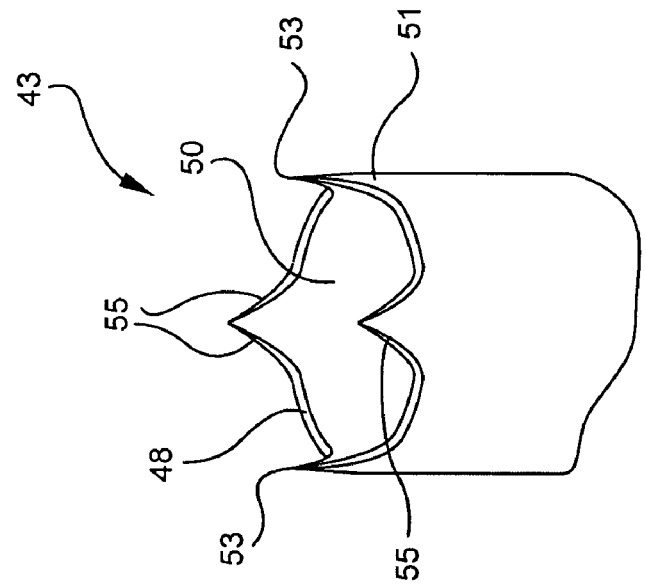
FIG. 14 is a perspective view of the distal end of the cutting element of FIG. 13.

A prior art cutting element 143 is illustrated in FIGS. 11 and 12. The cutting element includes a proximal end 145, a distal end 146 and a side wall 147 therebetween. Distal end 146 further includes a cutting edge 148. Prior art cutting elements are essentially cylindrical in form having a circular and planar cutting edge. The cutting edge is typically perpendicular to the longitudinal axis of the cutting element so that the cutting element's first contact with the inner surface of the stopper, or needle supporting element, depending on the design, is a full circular contact. When pressing against the stopper's interface the cutting mechanism is one of "chopping" wherein the cutter's circular edge penetrates directly into the stopper's inner surface. There is no sliding component to the cut. This type of action requires a very sharp edge so that the load required to make the cut is minimized. A sheet metal cutting element, depending on the manufacturing process used in its formation can be reasonably sharp as made. However, a post-forming sharpening process is required. Further, the cutter is hardened so that the very fine edge does not deform during the cutting process. Contact cutters tend to experience a wider range of cutting forces possibly associated with dimensional and material variations and cutter element sharpness. Forming the planar cutting edge at angle with respect to the longitudinal axis can reduce the chopping component of the cutting force.

The cutting element of the present invention offers a more robust design that does not necessarily require heat treatment or post-forming sharpening operations and reduces potential for having wide variations of forces required to achieve cutting of the stopper and the needle support structure. The cutting mechanism of the cutting element of the present invention is not primarily "chopping" but rather one of "piercing and shearing." The cutting edge geometry of the cutting element of the present invention is not a circular plane but rather pointed crown geometry. By changing the mechanism by which the cutter operates, the cutting force is reduced and so is the need for post-formation sharpening and heat treating.

Figure 15:
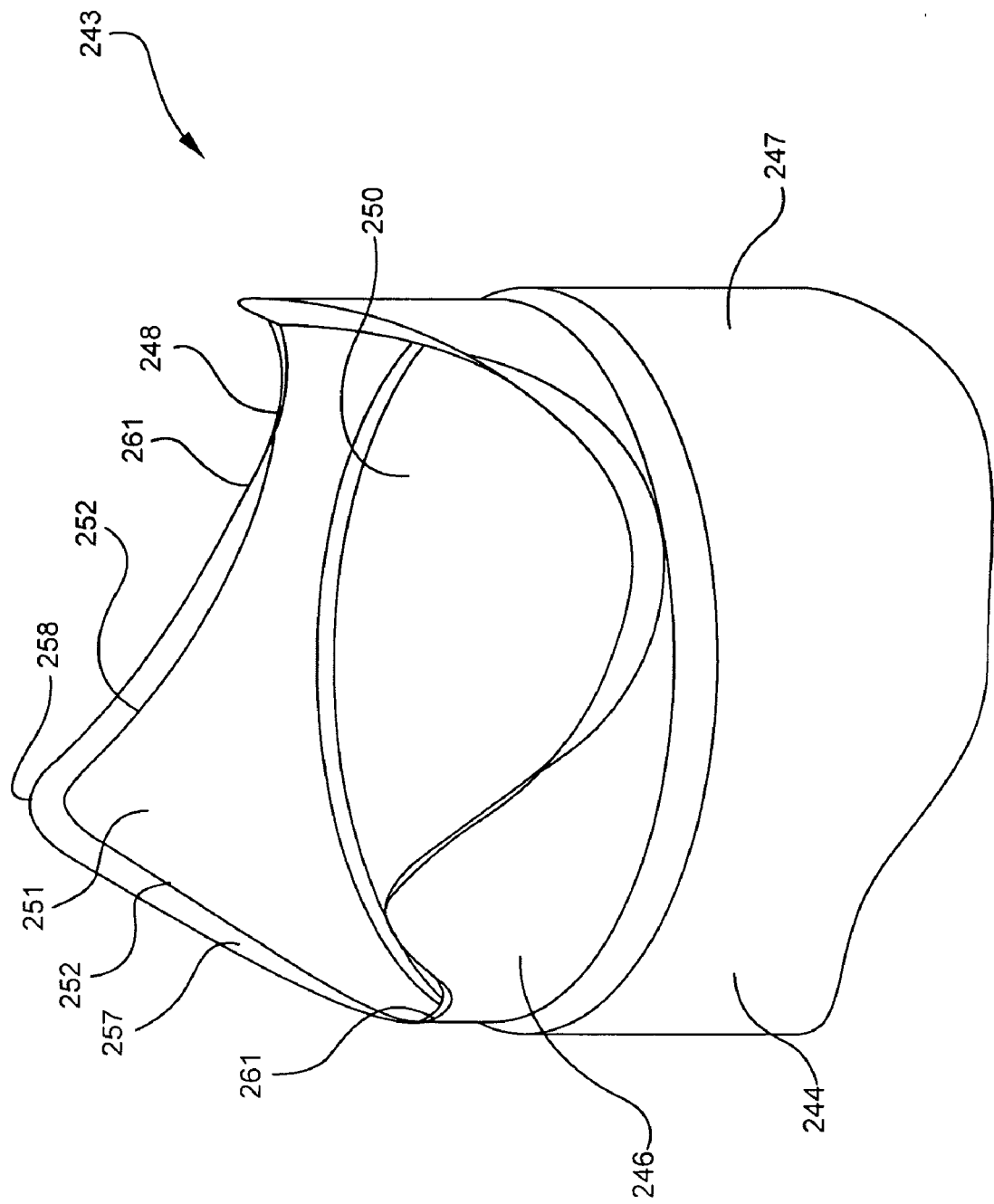
FIG. 15 is a perspective view of the distal end of a preferred cutting element for a retracting needle syringe of the present invention.

FIG. 15 illustrates the distal end of a preferred cutting element 243 of the present invention. Cutting element 243 includes a body portion 244 having a distal end 246 and a generally cylindrical side wall 247 defining a passageway 250 therethrough. The distal end includes cutting edge 248 and three distally projecting tapered cutting teeth 251 having distally converging edges 252. In this embodiment all three cutting teeth have a sharp side wall in the form of beveled edges 257. Each cutting tooth includes a distally directed point 258. The cutting teeth in this embodiment are substantially equally spaced around the distal end of the body portion and are separated by concave cutting edges 261, i.e., the cutting edge is concavely shaped in the spaces between the cutting teeth.

The pointed geometry of the teeth together with chiseled point profile of each of the points creates an initial contact against the target surface with very low surface area. When a force is applied, the load divided by the surface area defines the stress of penetration. Since the surface area is close to zero, the penetration stress is very high and capable of penetrating a target with only a very small load relative to prior art cutting elements. Once the penetration is established, the sharp beveled edges of the cutting teeth slice the target material rather than chop it. The applied forces is therefore administered over a longer distance along the longitudinal axis, thus requiring less force for equivalent work performed. Near the end of the cut, the target material is gathered between the roots of the cutting teeth, and the final portion of the cutting action indeed becomes a "chop," but the amount of material remaining is relatively small so that the force required to complete the cut is minimized.

The cutting element of the present invention can be tuned to provide a number of different feels while cutting based on the number of cutting teeth, the depth, the teeth, the form of the points, the form of the roots between the teeth and by formation of a chisel edge upon the profile of each cutting tooth. Based on these variations, a very soft feel, a very hard feel or countless interim feels can be produced.

Figure 16:
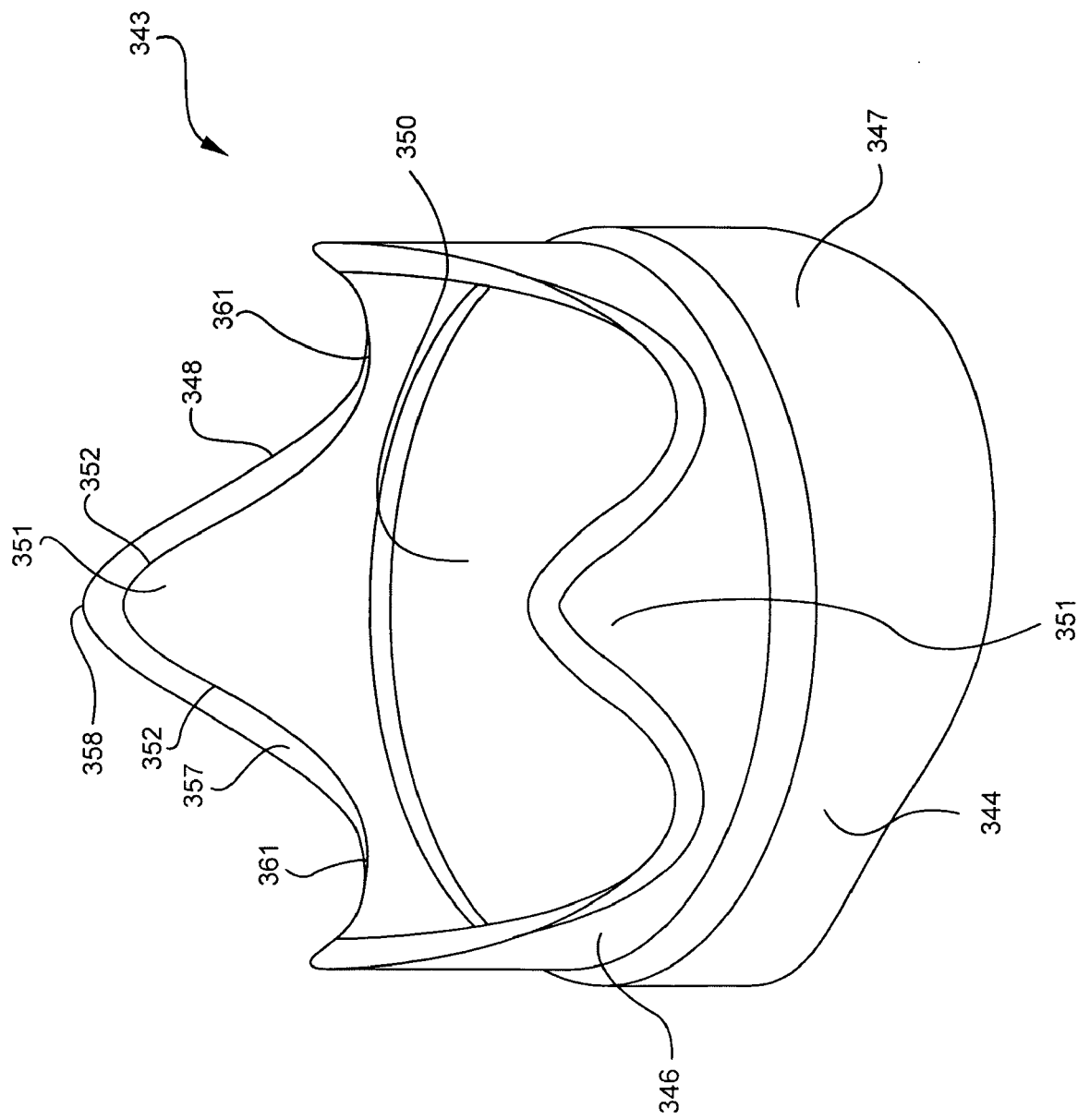
FIG. 16 is a perspective view of the distal end of an alternative cutting element of the present invention.

FIG. 16 illustrates an alternative cutting element of the present invention. In this embodiment cutting element 343 includes a body portion 344 having a distal end 346 and a generally cylindrical side wall 347 defining a passageway 350 therethrough. The distal end includes cutting edge 348 and four distally projecting tapered cutting teeth 351 having distally converging edges 352. In this embodiment all four cutting teeth have a sharp side wall in the form of beveled edges 357. Each cutting tooth includes a distally directed point 358. The cutting teeth in this embodiment are substantially equally spaced around the distal end of the body portion and are separated by concave cutting edges 361, i.e., the cutting edge is concavely shaped in the spaces between the cutting teeth.

Figure 17:
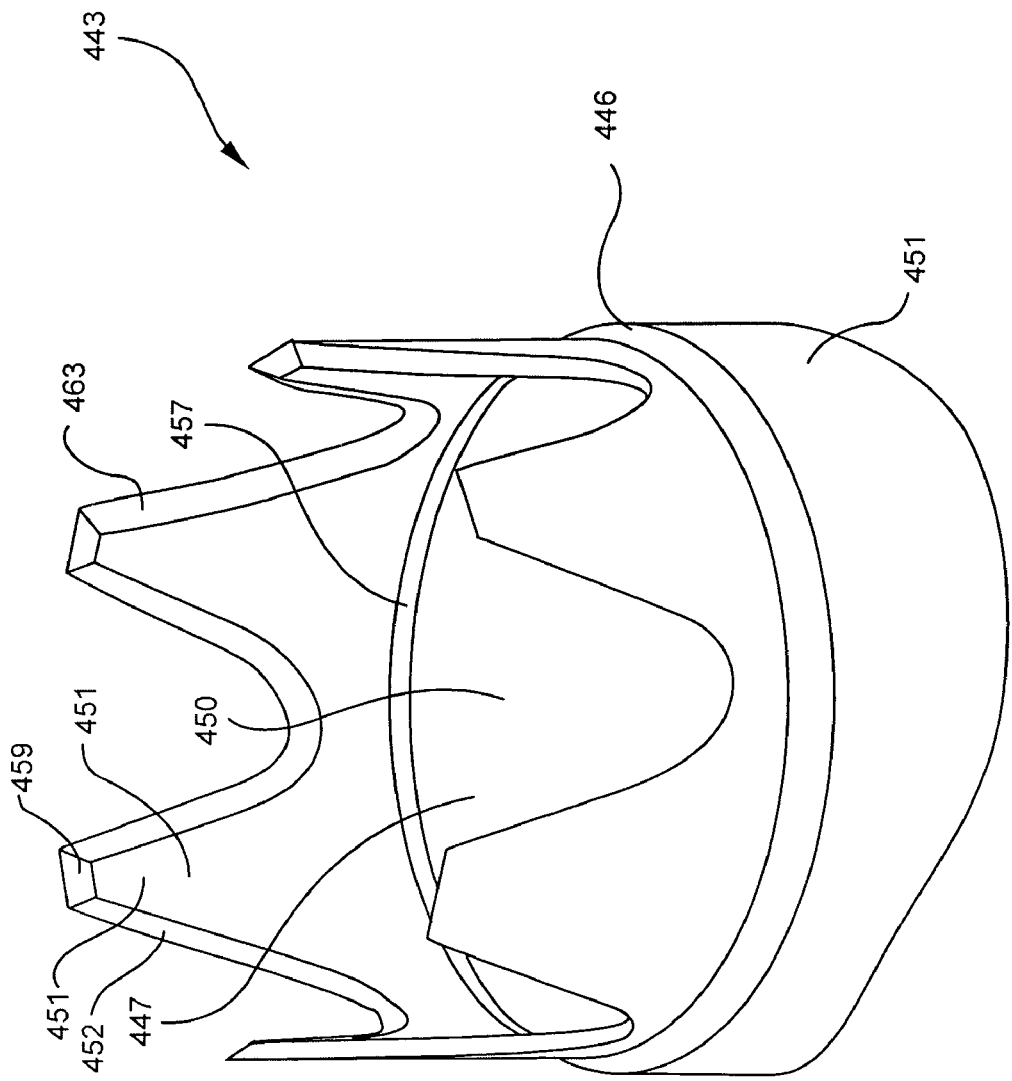
FIG. 17 is a perspective view of the distal end of another alternative cutting element of the present invention.

FIG. 17 illustrates another alternative embodiment of the present invention. In this embodiment, cutting element 443 includes a distal end 446, a side wall 447 and a passageway 450 through the cutting element. The cutting element in this embodiment includes six raised distally projecting tapered cutting teeth 451 having distally converging edges 452 terminating at a distally directed cutting edge 459. In this embodiment, all six cutting tooth edges have sharp side walls in the form of beveled edges 457. Distally directed cutting edge 459 also preferably includes a beveled cutting surface 463. The distally directed cutting edge may be desirable over a cutting point in situations where the force required to initiate cutting is desired to be higher than that possible with the pointed cutting tooth.

Figure 18:
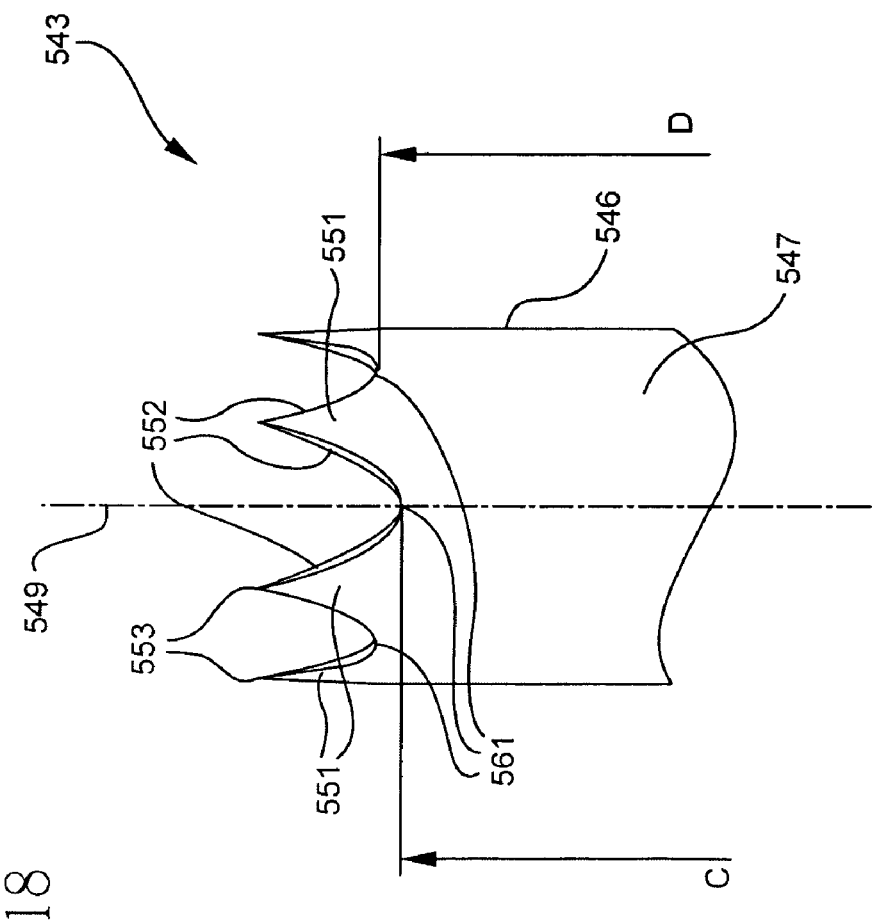
FIG. 18 is a side-elevational view of the distal end of still another alternative cutting element of the present invention.

As indicated hereinabove, near the end of the cut, the target material contacts the cutting edges between the cutting teeth wherein the final portion of the cutting action becomes a "chop". The amount of material remaining is relatively small so that the force required to complete the cut is minimized. The force is minimized even further by having the concave cutting edges which further reduce the amount of material that must be cut using a chopping action. The force of this final chopping action can also be reduced by staggering the cutting edges as illustrated in the embodiment of FIG. 18. In this embodiment, cutting element 543 includes a distal end 546, a side wall 547 and a passageway therethrough. The cutting element in this embodiment includes six raised distally projecting tapered cutting teeth 551 having distally converging edges 552 terminating at a distal tip 553. The cutting teeth in this embodiment are substantially equally spaced around the distal end of the body portion and are separated by concave cutting edges 561. At least two of the cutting edges between the cutting teeth are at different heights when measured along the longitudinal axis of the cutting element. In this embodiment, at least one cutting edge is positioned at distance C, measured along the longitudinal axis, while at least one other cutting edge is positioned at a different distance D, when measured along the longitudinal axis. Accordingly, the final minimal chopping action of the cutter is staggered to reduce the cutting force required. In this embodiment, every other cutting edge is at distance C and those cutting edges in between are at distance D.

Figure 19:
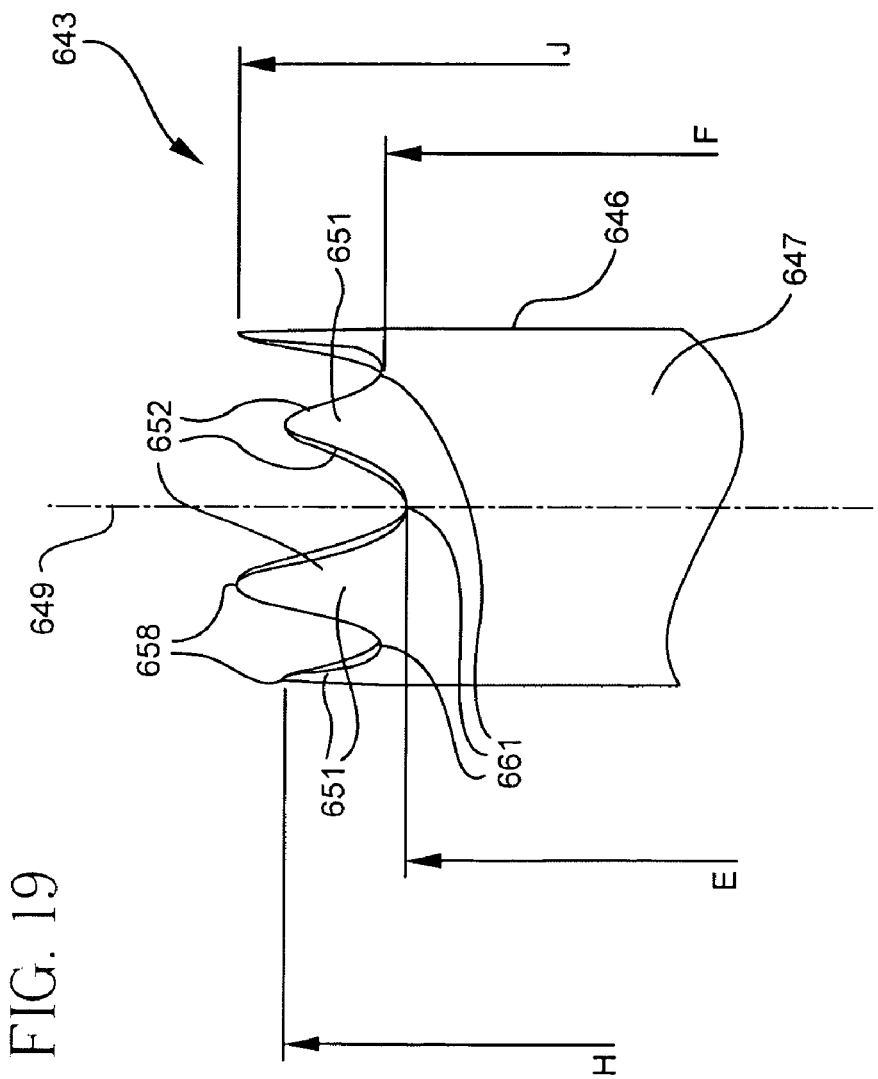
FIG. 19 is a side-elevational view of the distal end of another alternative cutting element of the present invention.

FIG. 19 illustrates another alternative embodiment of the present invention. This embodiment is similar to the embodiment of FIG. 18 except that the force required for the initial cutting action is reduced by staggering the distal tips of the cutting teeth. In this embodiment, cutting element 643 includes a distal end 646, a side wall 647 and a passageway therethrough. A cutting element in this embodiment includes six raised distally projecting tapered cutting teeth 651 having distally converging edges 652 terminating at distally directed point 658 at the distal tip. The cutting teeth in this embodiment are substantially equally spaced around the distal end of the body portion and are separated by concave cutting edges 661. At least two of the cutting edges between the cutting teeth are at different heights when measured along longitudinal axis 649 of the cutting element. In this embodiment, at least one cutting edge is positioned at distance E, measured along the longitudinal axis, while at least one other cutting edge is positioned at a different distance F, when measured along the longitudinal axis. Also, at least two of the distally directed points 558 are at different heights when measured along the longitudinal axis of the cutting element. In this embodiment, at least one distally directed point is positioned at distance H, measured along the longitudinal axis, while at least one other cutting edge is positioned at a different distance J, when measured along the longitudinal axis. Accordingly, staggering of the distally directed points 658 reduces the cutting force during this phase of cutting by not having all cutting action starting simultaneously.

It is desirable to make the cutting element out of metal such as sheet metal and preferably of stainless steel. However, any material suitable for cutting through the syringe components in question may be used to form the cutting element, such as plastic materials, ceramics and the like, all of which are within the purview of the present invention. The cutting element in the preferred embodiments for the present invention has a cylindrical side wall, however other shapes such as elliptical or multi-sides, such as hexagonal, square and the like are within the purview of the present invention and the cylindrical body portion illustrated is merely representative of these many possibilities.

Other retracting needle syringes such as retracting needle syringe taught in U.S. Pat. No. 6,432,087 B1 operate in a similar manner to the retracting needle syringe herein described but contain the cutting element in the distal end of the syringe barrel with the cutting edge facing in a proximal direction. In this type of retracting needle syringe, after the injection, the user provides an additional distally directed force to the plunger which causes the cutting element to cut through the support structure holding the energized spring and the needle and then through the distal end of the plunger to allow the spring to move the needle into the plunger cavity. The present cutting element is also intended to work in syringes of this type.

What is claimed is:

1. A cutting element for a retracting needle syringe having a plunger with a cuttable distal end and a spring biased needle held in an energized state by a cuttable support and said cutting element capable of cutting said cuttable distal end and said cuttable support comprising: a body portion having a proximal end, a distal end, a side wall therebetween defining a longitudinal axis and a passageway therethrough, said distal end including a cutting edge and a plurality of raised distally projecting tapered cutting teeth each having a distal tip and distally converging edges, at least one tooth edge having a sharp side wall for cutting said distal end of said plunger and said support, wherein at least two of said distal tips of said cutting teeth are at different heights when measured along said longitudinal axis.

2. A cutting element for a retracting needle syringe having a plunger with a cuttable distal end and a spring biased needle held in an energized state by a cuttable support and said cutting element capable of cutting said cuttable distal end and said cuttable support comprising: a body portion having a proximal end, a distal end, a side wall therebetween defining a longitudinal axis and a passageway therethrough, said distal end including a cutting edge and a plurality of raised distally projecting tapered cutting teeth each having a distal tip and distally converging edges, at least one tooth edge having a sharp side wall for cutting said distal end of said plunger and said support, wherein at least two of said cutting edges between said cutting teeth are at different heights when measured along said longitudinal axis.

3. A cutting element for a retracting needle syringe having a plunger with a cuttable distal end and a spring biased needle held in an energized state by a cuttable support and said cutting element capable of cutting said cuttable distal end and said cuttable support comprising: a body portion having a proximal end, a distal end, a side wall therebetween defining a longitudinal axis and a passageway therethrough, said distal end including a cutting edge and a plurality of raised distally projecting tapered cutting teeth each having a distal tip and distally converging edges, at least one tooth edge having a sharp side wall for cutting said distal end of said plunger and said support, wherein at least two of said distal tips of said cutting teeth are at different heights when measured along said longitudinal axis and at least two of said cutting edges between said cutting teeth are at different heights when measured along said longitudinal axis.

* * * * *